United States Patent [19]

Tobol

[11] Patent Number: 4,717,726

[45] Date of Patent: Jan. 5, 1988

[54] 3,5-DICHLORO-2,4-DIMETHOXY-6-(TRICHLOROMETHYL)PYRIDINE HAVING ANTI-TUMOR ACTIVITY

[75] Inventor: Helen K. Tobol, Concord, Calif.

[73] Assignee: The Dow Chemical Company, Midland, Mich.

[21] Appl. No.: 905,906

[22] Filed: Sep. 10, 1986

[51] Int. Cl.$^4$ ................. C07D 213/24; C07D 213/30; A61K 31/44

[52] U.S. Cl. ..................... 514/348; 546/296; 546/302

[58] Field of Search ......................... 546/296; 514/348

[56] References Cited

U.S. PATENT DOCUMENTS 4,190,662  2/1980  Fenstermacher et al. ...... 546/303 X

OTHER PUBLICATIONS

Remers Antineoplastic Agents, pp. 70–76, Wiley-Interscience Pub. 1984.

NIH Publication No. 84–2635, pp. 111, V, 5, 15, 23, 27, 31, "In Vivo Cancer Models" 1976–1982 Pub. NCI Feb. 1984.

*Primary Examiner*—Alan L. Rotman
*Attorney, Agent, or Firm*—D. Wendell Osborne

[57] ABSTRACT

3,5-Dichloro-2,4-dimethoxy-6-(trichloromethyl)-pyridine, which can be prepared from 2,3,4,5-tetrachloro-6-(trichloromethyl)pyridine and an alkali metal methoxide, is an anticancer agent especially useful for the treatment of leukemias, lymphomas, mammary carcinomas, and ovarian sarcomas.

10 Claims, No Drawings

3,5-DICHLORO-2,4-DIMETHOXY-6-(TRICHLOROMETHYL)PYRIDINE HAVING ANTI-TUMOR ACTIVITY

BACKGROUND OF THE INVENTION

The present invention relates to a novel compound, compositions containing the compound, the use of the compound in inhibiting the growth of malignant neoplasms in mammals, and a method of preparing the compound.

A number of chemicals that inhibit the growth or otherwise reduce or preclude the expansion of malignant neoplasms in mammals are known, but the discovery of additional chemicals possessing this activity, especially chemicals that are structurally unrelated to compounds presently known to possess this property, is highly desirable.

SUMMARY OF THE INVENTION

It has now been found that the novel compound, 3,5-dichloro-2,4-dimethoxy-6-(trichloromethyl)-pyridine, which can be depicted by the following formula:

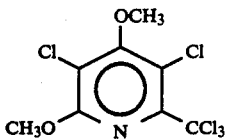

inhibits the growth of malignant neoplasms in afflicted mammals when administered in an amount effective to inhibit said growth. The spread of leukemias, of lymphomas, of mammary carcinomas, and of ovarian sarcomas is especially inhibited. The compound is usually administered in the form of a composition comprising an effective amount thereof and at least one pharmaceutically acceptable carrier or excipient.

3,5-Dichloro-2,4-dimethoxy-6-(trichloromethyl)pyridine can be prepared by combining 2,3,4,5-tetrachloro-6-(trichloromethyl)pyridine with about two or more molar equivalents of an alkali metal methoxide in an organic solvent under conditions conducive to the formation of 3,5-dichloro-2,4-dimethoxy-6-(trichloromethyl)pyridine as a reaction product and, thereafter, recovering said product. The reaction involved in the process can be depicted as follows:

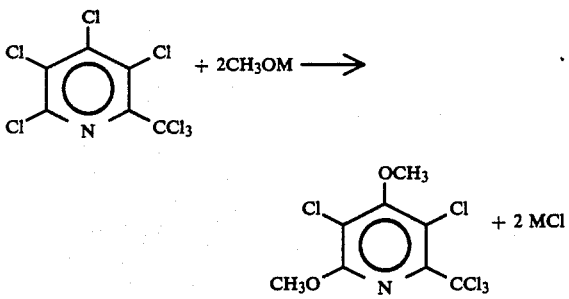

wherein M represents Na, K, or Li.

DETAILED DESCRIPTION OF THE INVENTION

The compound of the present invention, 3,5-dichloro-2,4-dimethoxy-6-(trichloromethyl)pyridine, inhibits the growth of malignant neoplasms or tumors in mammals. It is especially effective in preventing the spread of P388 lymphocytic leukemia and L-1210 lymphoid leukemia in mice and is, therefore, presumptively effective against leukemias and lymphomas, and possibly against some types of solid tumors, in other mammals including humans. It is further very effective against mammary carcinomas MX-1 and CD8F1 and ovarian sarcoma M5076 in mice and consequently is presumptively effective against mammary carcinomas and ovarian sarcomas in other mammals including humans and is likely effective against other related malignant neoplasms. Its use in humans is preferred.

3,5-Dichloro-2,4-dimethoxy-6-(trichloromethyl)pyridine can be administered to mammals parenterally, for example, by intraperitoneal (i.p.), subcutaneous (s.c.), or intravenous injection, or orally. It is preferred to administer it orally.

In use, an effective malignant neoplasm inhibiting dose of the compound is administered to an afflicted mammal. The exact amount of the compound to be employed; that is, the amount which is sufficient to inhibit the growth of susceptible malignant neoplasms, is not an absolute number, but depends on a variety of factors such as the species of mammal and its size and age, the method of administration and the time and frequency of administration, the specific malignant neoplasm present and its stage of development and the identity of any excipient used. The correct amount for any specific situation can be readily determined by those skilled in the art using conventional range finding techniques and by extrapolation of the results observed under other circumstances. The maximum amount employed is determined by the toxicology of the compound in the specific circumstances of administration and the minimum amount is determined by the on-set of malignant neoplasm growth inhibition activity.

The total amount of 3,5-dichloro-4,6-dimethoxy-6-(trichloromethyl)pyridine administered in a typical treatment to inhibit the growth of susceptible malignant neoplasms is preferably between about 60 mg/kg and about 2500 mg/kg for mice and between about 5 mg/kg and about 200 mg/kg for humans. This total amount is typically, but not necessarily, administered as a series of smaller doses over a period of about one day to about two months.

3,5-Dichloro-2,4-dimethoxy-6-(trichloromethyl)-pyridine is preferably administered in the form of a composition comprising the compound in admixture with one or more pharmaceutically acceptable carriers and excipients. "Pharmaceutically acceptable" carriers and excipients are substances that are chemically inert to the active compound and have no detrimental side effects or toxicity to mammals under the condition of use. Suitable carriers and excipients include solvents such as water, alcohol, and propylene glycol, solid absorbants and diluents, surface active agents, suspending agents, tableting binders, lubricants, flavors, colorants, and the like. Such carriers and excipients are known to those in the art and are disclosed, for example, in texts such as *Remington's Pharmaceutical Manufacturing*, 13th Edition, Mack Publishing Co., Easton, PA. (1965). The compositions may be liquids, such as suspensions or solutions, or solids, such as tablets, capsules, granulations, powders, and feed mixes, and may be designed for administration by injection or orally. Compositions designed for oral administration are preferred.

The concentration of the active ingredient, 3,5-dichloro-2,4-dimethoxy-6-(trichloromethyl)pyridine, in compositions useful for controlling the growth of malignant neoplasms and suitable for administration to mammals is a concentration at which a typically sized dose will be effective. Preferred compositions include those containing from about 0.0001 to about 60 percent by weight of the active compound. Those containing from about 0.001 to about 20 percent by weight are especially preferred.

The compound 3,5-dichloro-2,4-dimethoxy-6-(trichloromethyl)pyridine is readily prepared by the reaction of 2,3,4,5-tetrachloro-6-(trichloromethyl)pyridine, a well known intermediate, and about two or more equivalents of an alkali metal methoxide in an organic solvent medium. The order of addition of the reactants is not critical. The reaction is continued until a substantial quantity of the starting materials has been consumed or a substantial quanitity of the product has formed. The reaction is generally accelerated by heating and by agitation. At the conclusion of the reaction, the alkali metal chloride by-product, solvent, any remaining starting materials, and any co-products formed are removed by conventional techniques, such as filtration, extraction, distillation, crystallization, and the like. The product can be further purified by conventional methods including distillation and recrystallization from a solvent such as methanol, if desired.

The alkali metal methoxide employed can be sodium, potassium, or lithium methoxide. This can be preformed and added to the reaction medium either as a solid or as a solution in an organic solvent. Preformed solutions in methanol are preferred. The alkali metal methoxide can also be prepared in the reaction medium by the reaction of an alkali metal, an alkali metal hydroxide, or an alkali metal hydride with methanol as is known in the art either before or concurrently with the addition of 2,3,4,5-tetrachloro-6-(trichloromethyl)pyridine to the medium. The reaction consumes two molar equivalents of alkali metal methoxide for each mole of 2,3,4,5-tetrachloro-6-(trichloromethyl)pyridine employed. While some of the desired product is obtained when less than two molar equivalents are used, higher yields are obtained when about two are employed. Larger amounts of alkali metal methoxide can be employed successfully, but in this case, the reaction is preferably terminated before the desired product undergoes significant further reaction.

Suitable organic solvents for the process are those in which alkali metal methoxides are at least partially soluble and which are inert and do not degrade in the system. These include methanol, dimethyl sulfoxide, dimethylformamide, diglyme, tetrahydrofuran, and the like, and mixtures thereof. Methanol and mixtures of methanol with other solvents, especially dimethyl sulfoxide, are preferred.

The reaction phase of the process is generally carried out at about 40° C. to about 120° C. and preferably from about 40° C. to about 80° C. It is generally complete in about one hour to about ten hours at these temperatures.

The following examples are presented to illustrate various aspects of the invention and should not be construed as limiting the claims.

EXAMPLE 1—Preparation of 3,5-dichloro-2,4-dimethoxy-6-(trichloromethyl)pyridine

A 50.0 g portion (0.15 mol) of 2,3,4,5-tetrachloro-6-(trichloromethyl)pyridine was dissolved in 50 ml of warm dimethyl sulfoxide and 100 ml of methanol was added. Sodium methoxide (68.5 ml of 25 percent solution in methanol, 0.30 mol) was added, with stirring, over a 30 minute period and the resulting mixture was heated to reflux, with stirring, for two hours. After cooling, the mixture was poured into ice water and the aqueous mixture was extracted twice with methylene chloride. The extract was washed with water and evaporated to remove the methylene chloride. Traces of dimethyl sulfoxide remained. The residue was dissolved in ether and the ethereal solution was washed with water, dried over magnesium sulfate, and evaporated under reduced pressure to obtain 39.4 g of white solid product (81 percent of theory) melting at 67°–69° C. The proton nmr spectrum was consistent with the structure given.

| Analysis: | | | | |
|---|---|---|---|---|
| Calc. for $C_8H_6Cl_5NO_2$: | % C, 29.52; | % H, 1.86; | % N, 4.30; | % Cl, 54.5 |
| Found: | % C, 29.61; | % H, 1.73; | % N, 4.29; | % Cl, 54.7 |

EXAMPLE 2—Intraperitoneally-Implanted P388 Leukemia Test

The National Cancer Institute Protocol 3PS31 was employed. In this test, $CD_2F_1$ mice weighing about 18 grams are implanted i.p. with about one million P338 leukemia cells in ascitic fluid. A group of six of these mice are treated the following day and each of the next four days with the test compound by i.p. injection. Positive and untreated controls are maintained. The median survival times of the test mice and the untreated control mice are measured. Compounds that give a median survival time of greater than 120 percent of the untreated control are considered to be active. 3,5-Dichloro-2,4-dimethoxy-6-(trichloromethyl)pyridine at 1000 (five 200 mg/kg doses) and at 675 (five 135 mg/kg doses) mg/kg body weight gave increases of 194 and 196 percent, respectively.

EXAMPLE 3—Intraperitoneally-Implanted L1210 Leukemia Test

The National Cancer Institute Protocol 3LE31 was employed. In this test, $CD_2F$ or $B_6D_2F$ mice weighing about 18 grams are implanted i.p. with about 100,000 L1210 leukemia cells in ascitic fluid. One day later and on the following eight days, a group of six mice is treated with the test compound by i.p. injection. Positive and untreated controls are maintained. The median survival time of the test mice and the untreated control mice are measured. Compounds that give a median survival time greater than 125 percent of the untreated control are considered to be active. 3,5-Dichloro-2,4-dimethoxy-6-(trichloromethyl)pyridine at 900 mg/kg (nine 100 mg/kg doses) mg/kg body weight gave increases of 146 and 130 percent in two tests.

EXAMPLE 4—Subcutaneously-Implanted Staged Mammary Adenocarcinoma CD8F1 Test

The National Cancer Institute Protocol 3CDJ2 was employed. In this test, CD8F1 mice weighing about 18 grams are implanted s.c. in the auxillary region with a 1:20 tumor brei. On staging day (more than two days after implanting), mice having tumors weighing between 100 mg and 700 mg are selected and the tumors are measured with calipers. A group of ten is weighed and treated with the test compound i.p. Positive and untreated controls are maintained. After seven days the group is weighed and the tumors measured with calipers. Tumor weights on staging day and after seven days are estimated from the measurements assuming prolate ellipsoids and the changes in tumor weight (final-initial) are calculated. Compounds giving less than 20 percent as much tumor growth as the untreated controls are considered active. 3,5-Dichloro-2,4-dimethoxy-6-(trichloromethyl)pyridine at 1000 and at 500 mg/kg body weight gave actual decreases in tumor weight of −58 and −28 percent, respectively.

EXAMPLE 5—Subrenal Capsule Human Mammary Carcinoma MX-1 Xenograph Test

The National Cancer Institute Protocol 3MBG5 was employed. In this test, athymic Swiss or athymic random bred mice weighing about 18 grams are implanted with a tumor fragment under the membranous covering of the kidney. The size of the tumor is measured. On the next day, a group of six mice is treated with the test compound by i.p. injection in the nape of the neck. Positive and untreated controls are maintained. Further injections of the test compounds are given to the test animals every fourth day for a total of three injections. After 11 days, body weights and tumor sizes are measured for all animals. Tumor weights are estimated from length and width measurements by assuming prolate ellipsoids and the changes in tumor weight (final-initial) are calculated. Compounds giving less than 20 percent as much tumor growth as the untreated controls are considered active. 3,5-Dichloro-2,4-dimethoxy-6-(trichloromethyl)pyridine at 900 (three 300 mg/kg doses) and at 450 (three 150 mg/kg doses) mg/kg body weight gave actual decreases in tumor weight of −53 and −48 percent, respectively.

In an essentially identical test in which the chemical is administered orally instead of i.p., the subject compound at 900 (three 300 mg/kg doses) and at 450 (three 150 mg/kg doses) mg/kg body weight gave actual decreases in tumor weight of −15 and −33 percent, respectively.

EXAMPLE 6—M5076 Ovarian Sarcoma Test

The National Cancer Institute Protocol 3M531 was employed. In this test, $B_6C_3F_1$ mice weighing about 18 grams are implanted i.p. with about 1 million M5076 tumor cells in ascitic fluid. A group of ten of these mice are treated the following day and every fourth day thereafter (total of four doses) with the test compound i.p. Positive and untreated controls are maintained. The median survival times of the test and control mice are measured. Compounds that give a median survival time increase of greater than 125 percent over the untreated control are considered to be active. 3,5-Dichloro-2,4-dimethoxy-6-(trichloromethyl)pyridine at 1600 (four 400 mg/kg doses) and at 716 (four 179 mg/kg doses) mg/kg body weight exhibited an increased median survival time of 168 and 152 percent respectively.

What is claimed is:
1. 3,5-Dichloro-2,4-dimethoxy-6-(trichloromethyl)pyridine.
2. A composition useful for inhibiting the growth of susceptible malignant neoplasms in mammals which comprises an effective amount of 3,5-dichloro-2,4-dimethoxy-6-(trichloromethyl)pyridine in combination with at least one pharmaceutically acceptable carrier or excipient.
3. A composition according to claim 2 designed for oral administration to humans.
4. A method for inhibiting the growth of a susceptible malignant neoplasm selected from the group consisting of leukemia, lymphoma, mammary carcinoma, or ovarian sarcoma in a mammal afflicted therewith which comprises administering to said mammal, in an amount effective to inhibit said growth, the compound 3,5-dichloro-2,4-dimethoxy-6(trichloromethyl)pyridine.
5. A method according to claim 4 wherein the malignant neoplasm is a leukemia.
6. A method according to claim 4 wherein the malignant neoplasm is lymphoma.
7. A method according to claim 4 wherein the malignant neoplasm is mammary carcinoma.
8. A method according to claim 4 wherein the malignant neoplasm is ovarian sarcoma.
9. A method according to claim 4 wherein the 3,5-dichloro-2,4-dimethoxy-6-(trichloromethyl)pyridine is administered orally.
10. A method according to claim 4 wherein the mammal is a human.

* * * * *